(12) United States Patent
Nash et al.

(10) Patent No.: US 8,016,799 B2
(45) Date of Patent: Sep. 13, 2011

(54) CATHETER HAVING A DETACHABLE TIP

(75) Inventors: Stephen Nash, Newcastle West (IE);
Patricia O'Beirne, Roscam (IE); David Johnson, Ballybrit (IE); Stephen Gormley, Ballybrit (IE); Grace Kelly, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 613 days.

(21) Appl. No.: 12/107,527

(22) Filed: Apr. 22, 2008

(65) Prior Publication Data
US 2009/0264858 A1    Oct. 22, 2009

(51) Int. Cl.
*A61M 5/32* (2006.01)
(52) U.S. Cl. ....................................... 604/265
(58) Field of Classification Search ........... 604/523, 604/93.01, 264–266; 606/195
See application file for complete search history.

(56) References Cited

U.S. PATENT DOCUMENTS

| | | | |
|---|---|---|---|
| 4,636,195 A | 1/1987 | Wolinsky | |
| 5,827,242 A | 10/1998 | Follmer et al. | |
| 6,066,156 A * | 5/2000 | Yan | 606/192 |
| 6,197,324 B1 | 3/2001 | Crittenden | |
| 6,251,418 B1 | 6/2001 | Ahern et al. | |
| 6,379,334 B1 * | 4/2002 | Frassica | 604/165.04 |
| 6,394,956 B1 | 5/2002 | Chandrasekaran et al. | |
| 6,569,129 B1 * | 5/2003 | Holmes et al. | 604/264 |
| 6,673,058 B2 | 1/2004 | Snow | |
| 6,800,085 B2 | 10/2004 | Selmon et al. | |
| 2004/0143321 A1 * | 7/2004 | Litvack et al. | 623/1.42 |
| 2004/0204672 A1 | 10/2004 | Palasis et al. | |
| 2005/0053548 A1 | 3/2005 | Strauss | |
| 2005/0209559 A1 | 9/2005 | Thornton et al. | |
| 2005/0216044 A1 | 9/2005 | Hong | |
| 2005/0245637 A1 | 11/2005 | Hossainy et al. | |
| 2007/0014783 A1 | 1/2007 | Strauss | |
| 2007/0184083 A1 * | 8/2007 | Coughlin | 424/422 |

OTHER PUBLICATIONS

US 6,056,969, 05/2000, Crittenden (withdrawn)

* cited by examiner

*Primary Examiner* — Theodore J Stigell
*Assistant Examiner* — Bradley J Osinski (57) ABSTRACT

A catheter is disclosed that has a detachable tip for delivery of a therapeutic substance to a chronic total occlusion (CTO) within a body vessel. The tip is made from a biodegradable material and includes an active agent dispersed therethrough. The detachable tip pierces into the calcified lesion, detaches from the catheter, and remains embedded within the lesion as the tip degrades, thereby releasing the active agent. The active agent is a therapeutic substance effective to treat of a CTO. The active agent may be a drug, an enzyme, bacteria, or a parasite that degrades or softens the calcified lesion.

17 Claims, 4 Drawing Sheets

CATHETER HAVING A DETACHABLE TIP

FIELD OF THE INVENTION

The invention relates generally to intraluminal devices for the treatment of a chronic total occlusion (CTO), and more particularly, to a catheter having a detachable tip for delivery of a therapeutic substance within a CTO.

BACKGROUND OF THE INVENTION

Stenotic lesions may comprise a hard, calcified substance and/or a softer thrombus material, each of which forms on the lumen walls of a blood vessel and restricts blood flow. Intraluminal treatments such as balloon angioplasty, stent deployment, atherectomy, and thrombectomy are well known and have proven effective in the treatment of such stenotic lesions. These treatments often involve the insertion of a therapy catheter into a patient's vasculature, which may be tortuous and may have numerous stenoses of varying degrees throughout its length. In order to place the distal end of a catheter at the treatment site, a guidewire is typically introduced and tracked from an incision, through the vasculature, and across the lesion. Then, a balloon catheter, perhaps containing a stent at its distal end, can be tracked over the guidewire to the treatment site. Ordinarily, the distal end of the guidewire is quite flexible so that it can be rotatably steered and pushed through the bifurcations and turns of the typically irregular passageway without damaging the vessel walls.

In some instances, the extent of occlusion of the lumen is so severe that the lumen is completely or nearly completely obstructed, which may be described as a total occlusion. If this occlusion persists for a long period of time, the lesion is referred to as a chronic total occlusion or CTO. Furthermore, in the case of diseased blood vessels, the lining of the vessels may be characterized by the prevalence of atheromatous plaque, which may form total occlusions. The extensive plaque formation of a chronic total occlusion typically has a fibrous cap surrounding softer plaque material. This fibrous cap may present a surface that is difficult to penetrate with a conventional guidewire, and the typically flexible distal tip of the guidewire may be unable to cross the lesion.

Thus, for treatment of total occlusions, stiffer guidewires have been employed to recanalize through the total occlusion. However, due to the fibrous cap of the total occlusion, a stiffer guidewire still may not be able to cross the occlusion and may prolapse into the vessel when force is applied. When using a stiffer guidewire, great care must be taken to avoid perforation of the vessel wall.

Further, even if the guidewire can penetrate the proximal cap of the total occlusion, it may not be able to completely cross the occlusion. In a CTO, there may be a distortion of the regular vascular architecture such that there may be multiple small non-functional channels throughout the occlusion rather than one central lumen for recanalization. Thus, the conventional approach of looking for the single channel in the center of the occlusion may account for many of the failures. Furthermore, these spontaneously recanalized channels may be responsible for failures due to their dead-end pathways and misdirecting of the guidewires. Once a "false" tract is created by a guidewire, subsequent attempts with different guidewires may continue to follow the same incorrect path, and it is very difficult to steer subsequent guidewires away from the false tract.

Another equally important failure mode, even after a guidewire successfully crosses a chronic total occlusion, is the inability to advance a balloon or other angioplasty equipment over the guidewire due to the fibrocalcific composition of the chronic total occlusion, which occurs mainly at the "entry" and "exit" segments of the chronic total occlusion.

Due to the issues described above, there is a need in the art for improved devices and methods for treatment of a CTO.

BRIEF SUMMARY OF THE INVENTION

Embodiments of the present invention relate to a device for treatment of a chronic total occlusion. The device includes a catheter having a proximal end and a distal end. A detachable tip is attached to the distal end of the catheter, the tip being formed out of a biodegradable polymer with an active agent dispersed therethrough, the active agent being effective to soften or degrade at least a portion of the chronic total occlusion. The device also includes a detachment mechanism for detaching the tip from the distal end of the catheter.

BRIEF DESCRIPTION OF DRAWINGS

The foregoing and other features and advantages of embodiments of the present invention will be apparent from the following description as illustrated in the accompanying drawings. The accompanying drawings, which are incorporated herein and form a part of the specification, further serve to explain the principles of the invention and to enable a person skilled in the pertinent art to make and use embodiments hereof. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments of the present invention are directed to a catheter having a detachable tip for treatment of a CTO. In an embodiment, the tip is made from a biodegradable material and an active agent that attacks the calcified material in a lesion. The tip pierces into the occlusion, detaches from the catheter, and remains embedded within the lesion as it degrades, thereby releasing the active agent. Thus, the detachable tip may be used for precise delivery of a therapeutic material directly to the CTO. Such direct delivery has many advantages, including that the active agent does not have to travel to the areas of interest. Thus, the amount of required active agent for effectively attacking the CTO is reduced since it is delivered directly to the target site. In addition, substances previously not considered for treatment of a calcified lesion due to the potential of harm to other organs may be utilized. Further details and description of embodiments are provided below with reference to FIGS. 1-15.

Figure 1:
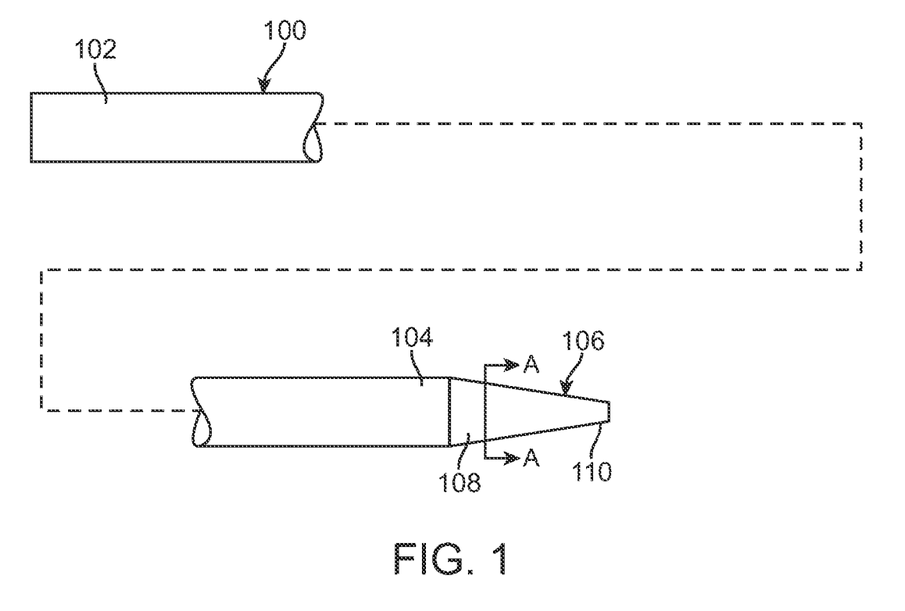
FIG. 1 is a schematic side view of a catheter having a detachable tip according to an embodiment of the present invention.
Figure 1A:
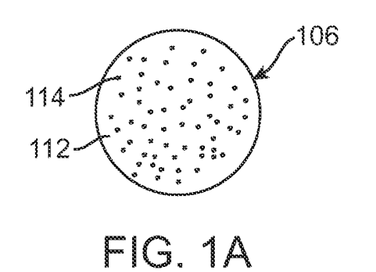
FIG. 1A is a cross-sectional view taken along line A-A of FIG. 1.

FIG. 1 is a schematic side view of a catheter 100 having a detachable tip 106, with FIG. 1A showing a cross-sectional view of tip 106 taken along line A-A in FIG. 1. Catheter 100 includes a proximal end 102 that extends out of the patient and may be manipulated by a clinician, and a distal end 104 positionable at a target location within the vasculature. Catheter 100 may include an extruded shaft formed of any suitable flexible polymeric material. Non-exhaustive examples of material for catheter 100 are silicone, polyethylene terephalate (PET), nylon, polyethylene, PEBAX, or combinations of any of these, either blended or co-extruded. Optionally, a portion of the catheter may be formed as a composite having a reinforcement material incorporated within a polymeric body in order to enhance strength, flexibility, and/or toughness. Suitable reinforcement layers include braiding, wire mesh layers, embedded axial wires, embedded helical or circumferential wires, and the like. In an embodiment, the proximal portion of the catheter may in some instances be formed from a reinforced polymeric tube, for example, as shown and described in U.S. Pat. No. 5,827,242 to Follmer et al. which is incorporated by reference herein in its entirety. The catheter may have any suitable working length, for example, 550 mm-650 mm, in order to extend to a target location within the vasculature.

Figure 3:
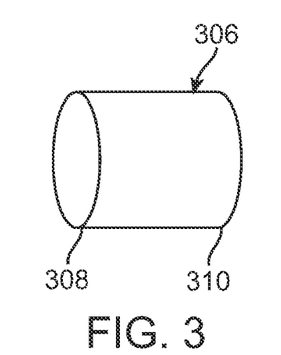
FIG. 3 is a schematic of a detachable tip according to another embodiment of the present invention.

Detachable tip 106 is attached to distal end 104 of catheter 100. Tip 106 includes a proximal end 108 having a first outer diameter and a distal end 110 having a second outer diameter. Tip 106 includes a geometry that is capable of piercing into a CTO and has the structural integrity to maintain this geometry. However, if tip 106 is unable to pierce the proximal fibrous cap of the CTO, it may alternatively be advanced through a channel created within the CTO by a ROTABLATOR, manufactured by Boston Scientific Corporation. In the embodiment shown in FIG. 1, the first outer diameter is greater than the second outer diameter such that tip 106 has a tapered or conical configuration as it extends distally. Although tip 106 has been shown as a frusto-conical structure, the tip can take on different suitable configurations, such as a pointed or rounded distal end 110 (not shown). In addition, FIG. 3 shows an alternate tip configuration. A detachable tip 306 has a cylindrical configuration in which the first outer diameter of proximal end 308 is approximately equal to the second outer diameter of distal end 310. The profile of cylindrical tip 306 is similar to that of a typical guidewire, which is about 0.014 inches to about 0.020 inches.

As shown in FIG. 1A, detachable tip 106 may be constructed out of a solid polymer matrix 112 having an active agent 114 dispersed therethrough. The solid polymer matrix provides tip 106 with high strength for ease of introduction within a CTO. Polymer matrix 112 is a biodegradable polymer that dissolves or breaks down within a vessel such that active agent 114 is released or emitted into a CTO for treatment thereof. The biodegradable polymer may include, for example, chitosan, caprolactone, modified cellulose, collagen, albumin, casein, polysaccharides (PSAC), polylactide (PLA), polylactide[poly-L-lactide (PLLA), poly-D-lactide (PDLA)], polyglycol (PGA), poly-D,L-lactide-co-glycolide (PDLLA/PGA), polyhydroxybutyric acid (PHB), polyhydroxyvaleric acid (PHV), polyalkylcarbonate, polyorthoester, polyethylene terephthalate (PET), polymalic acid (PMLA), polyanhydrides, polyphosphazenes, polyamino acids or related copolymers materials. Each type of biodegradable polymer has a characteristic degradation rate in the body. The dissolution rate of tip 106 may be tailored by controlling the type of biodegradable polymer, the thickness and/or density of the biodegradable polymer, and/or the nature of the biodegradable polymer. In addition, characteristics such as the chemical composition and molecular weight of the biodegradable polymer may also be selected in order to control the dissolution rate of tip 106.

Figure 2:
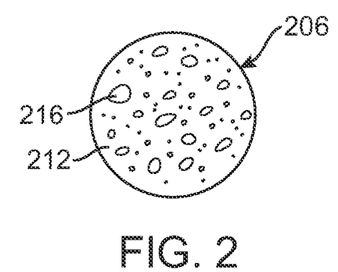
FIG. 2 is a cross-sectional view taken according to another embodiment of the present invention.

In another embodiment of the invention, as shown in FIG. 2, tip 206 has a polymer matrix 212 that includes pores 216 disposed throughout the matrix. Although not shown in FIG. 2, pores 216 include active agent 114 dispersed therein. Since a porous material has a higher surface area than a solid material, if tip 206 is made of the same biodegradable material as tip 106, than tip 206 will provide faster dissolution of active agent 114 and possibly more uniform biodegradation of the tip. Similar to the solid tip embodiment above, the active agent will be released as the biodegradable material of the tip degrades. In addition or alternatively, due to tip 206 being porous, the active agent may also be released through diffusion. More particularly, controlled release of the active agent may occur as the active agent moves from areas of higher concentration, i.e., within the porous tip material, to areas of lower concentration, i.e., within the occlusion. Controlled release of the active agent into the lesion may thus occur through a combination of degradation and diffusion.

Active agent 114 is a therapeutic substance that softens or degrades the material of a CTO. Atherosclerotic plaques vary considerably in their composition from site to site, but certain features are common to all of them, such as plaques contain many cells, which mostly are derived from cells of the wall that have divided and grown into the surface layer of the blood vessel, creating a mass lesion. Plaques also contain cholesterol and cholesterol esters, commonly referred to as fat, which may lie freely in the space between the cells and in the cells themselves. A large amount of collagen is also present in the plaques, particularly advanced plaques of the type which cause clinical problems such as CTO. Additionally, human plaques contain calcium to varying degrees, hemorrhagic material including clot and grumous material composed of dead cells, and other debris. Relatively large amounts of water are also present, as is typical of all tissue. In various embodiments, active agent 114 is a drug, an enzyme, bacteria, or a parasite that degrades or "eats" the calcified lesion. In another embodiment, active agent 114 is a drug, an enzyme, bacteria, or a parasite that softens the calcified lesion to allow for secondary intervention such as a balloon angioplasty and/or stenting.

As mentioned, active agent 114 may be an enzyme that softens or degrades the material of a CTO. The enzyme is preferably one that acts locally to specifically degrade the collagen content of the CTO, as collagen is a predominant component of atherosclerotic plaque and is a main supportive structure of plaque of a CTO, so that the plaque body then collapses. Suitable examples include, but are not limited to, "proteolytic enzyme-containing formulations" as described in U.S. Published Patent Application Publication No. 2005/0053548, which is incorporated by reference herein in its entirety. The proteolytic enzyme may be selected from: matrix metalloproteinases, serine elastases, trypsin, neutral protease, chymotrypsin, aspartase, cysteinase and clostripain. Matrix metalloproteinases (MMPs) is a group of zinc-containing enzymes that are responsible for degradation of extracellular matrix (ECM) components, including collagen, fibronectin, elastin, proteoglycans and laminin. These ECM components are important components of the occluding atherosclerotic plaque. MMPs play an important role in normal embryogenesis, inflammation, wound healing and tumour invasion. These enzymes are broadly classified into three general groups: collagenases, gelatinases and stromelysins. Collagenase is the initial mediator of the extracellular pathways of interstitial collagen degradation, with cleavage at a specific site in the collagen molecule, rendering it susceptible to other neutral proteases (e.g. gelatinases) in the extracellular space. In one embodiment, the proteolytic enzyme containing formulation includes a matrix metalloproteinase selected from: collagenase, type 1A collagenase, gelatinases, and stromelysins. In another embodiment, the proteolytic enzyme containing formulation includes collagenase, whether alone or in combination with other enzymes. The enzyme may be "temperature-activated" such that the collagen-degrading properties thereof are not in effect until the tip is located in situ.

In yet another embodiment, active agent 114 is bacteria that softens or degrades the material of a CTO. The bacteria preferably acts locally to specifically degrade the collagen content of the CTO so that the plaque body then collapses. Bacteria may degrade the lesion directly or create a byproduct, such as an enzyme, that will act on the lesion. Suitable examples include, but are not limited to, porphyromonas gingivalis, treponema denticola or other bacteria capable for degrading collagen of a CTO. Since the bacteria are delivered directly to the site of the CTO, they would act to clear the blockage before a patient's immune system destroyed them. In addition, if necessary, the bacteria may be counteracted by an antibiotic or other remedy once the blockage is cleared.

In another embodiment, active agent 114 is a drug that softens or degrades the material of a CTO. The drug is preferably one that acts locally to specifically degrade the collagen content of the CTO so that the plaque body then collapses. Suitable examples include, but are not limited to, sirolimus, paclitaxul, or other drugs capable of degrading collagen of a CTO.

In yet another embodiment, active agent 114 is a parasite that degrades the material of a CTO by feeding on the calcified lesion. A parasite may degrade the lesion directly or create a byproduct, such as an acid or enzyme, that will act on the lesion. Since the parasite is delivered directly to the site of the CTO, it would act to clear the blockage before a patient's immune system destroys it. In addition, if necessary, the parasite may be counteracted by an anti-parasitic or other remedy once the blockage is cleared.

Figure 4:
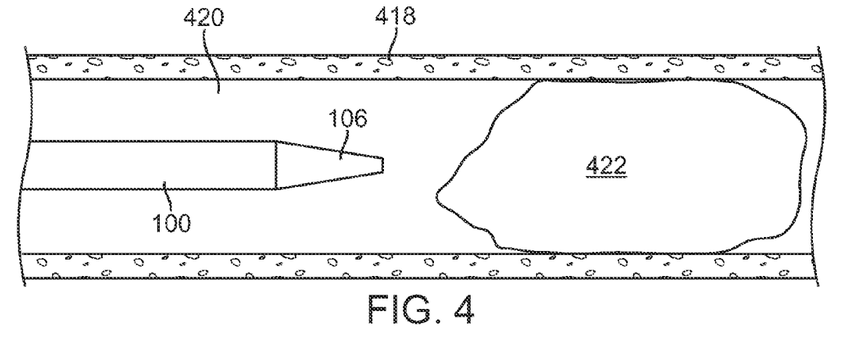
FIGS. 4-7 diagrammatically illustrate the steps of a method of deploying the detachable tip within a chronic total occlusion.
Figure 5:
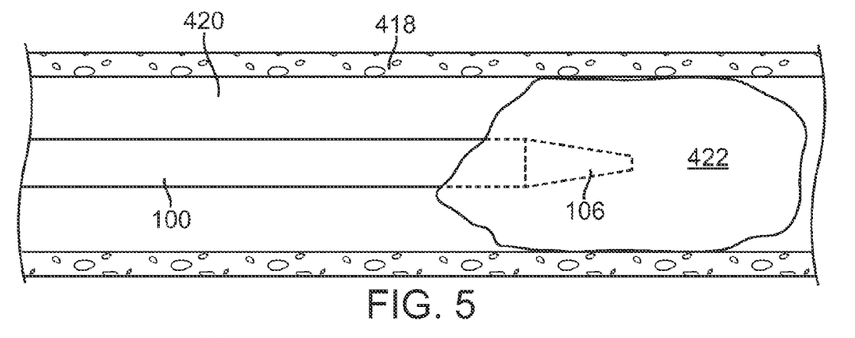

FIGS. 4-7 diagrammatically illustrate the steps of a method of deploying detachable tip 106 within a chronic total occlusion 422 located within a body lumen 420 of a blood vessel 418. Typically, a guiding catheter is first inserted through an incision (not shown) and into a femoral artery of a patient. Catheter 100 is then advanced through the guiding catheter, into the patient's aorta and then into the ostium of the selected artery or vessel. As shown in FIG. 4, catheter 100 is positioned by a clinician such that detachable tip 106 is proximally adjacent to occlusion 422 in vessel 418. Referring to FIG. 5, detachable tip 106 pierces and is pushed into occlusion 422. If tip 106 is unable to pierce the proximal fibrous cap of occlusion 422, a channel (not shown) may be previously created within occlusion 422 by a ROTABLATOR in order to facilitate advancement of the tip within the CTO.

Figure 6:
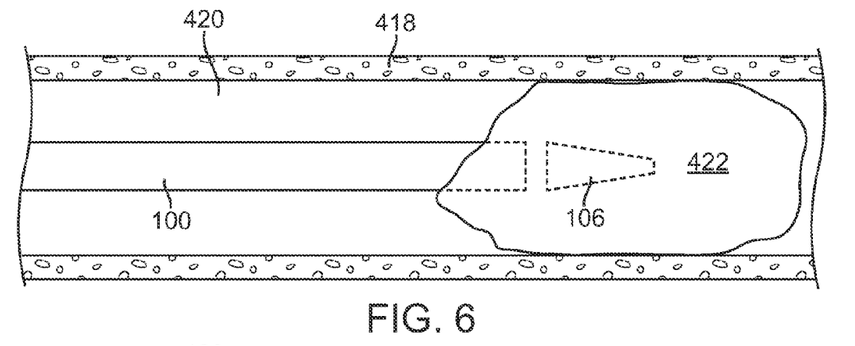
Figure 7:
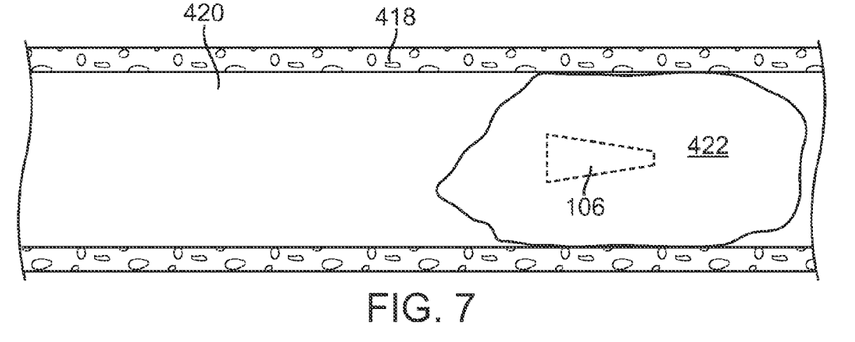

As shown in FIG. 6, once in place within occlusion 422, detachable tip 106 detaches from catheter 100 via a detachment mechanism. As explained in more detail below, the detachment mechanism may be any mechanism capable of effectively separating tip 106 from the remainder of catheter 100. For example, the detachment mechanism may include a pressure source, an inflatable balloon, a temperature sensitive adhesive, a screw-like mating arrangement, or a tip geometry capable of lodging the tip into the occlusion. Catheter 100 is proximally retracted and withdrawn, while detached tip 106 remains in occlusion 422 as shown in FIG. 7. As polymer matrix 112 biodegrades, active agent 114 is released to soften or degrade occlusion 422. If active agent 114 merely softens occlusion 422, a conventional recanalization catheter procedure is subsequently performed, such as balloon angioplasty and/or stenting. Due to the softening or dissolution of at least a portion of occlusion 422, a guidewire, and subsequently the treatment catheter, can pass through occlusion 422 for such a conventional recanalization procedure.

As previously mentioned, the detachable tip detaches from catheter via a detachment mechanism. In one embodiment, the catheter shaft may be formed of a low surface energy material, such as silicone, that can be unprimed or primed to achieve a level of adhesion between the catheter shaft and the detachable tip that is sufficient to track the device to CTO but that can be detached or broken via the detachment mechanism.

Figure 8:
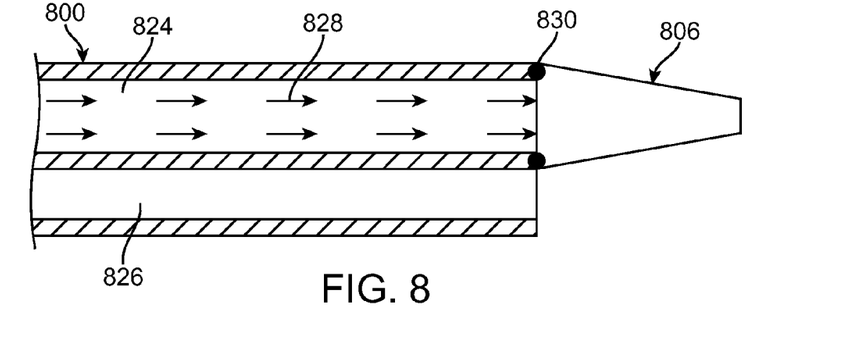
FIG. 8 is a schematic sectional view of a catheter having a deployment mechanism according to an embodiment of the present invention, wherein the deployment mechanism includes a pressure source.

In one embodiment, the detachment mechanism includes a pressure source to effectively break the bond between the tip and the catheter, thus expelling the tip. As shown in FIG. 8, tip 806 is attached to catheter 800 via a bond 830. Bond 830 may be formed with an adhesive, a solvent bond, a thermal bond, a connecting element between catheter 800 and tip 806, a room temperature vulcanised overcoat that cures over catheter 800, or by another mechanical method. Pressure, as indicated by directional arrows 828, is provided through an inflation lumen 824 of catheter 800 via a pressure source (not shown) attached to the proximal end of the catheter. Within a certain pressure window, bond 830 fails, effectively detaching tip 806 from catheter 800 and leaving tip 806 within the CTO. The force necessary to expel tip 806 from catheter 800 may be supplied by pressurized gas or air, pressurized liquids such as water or saline, and/or the use of a push structure advanced through lumen 824 of catheter 800.

Figure 9:
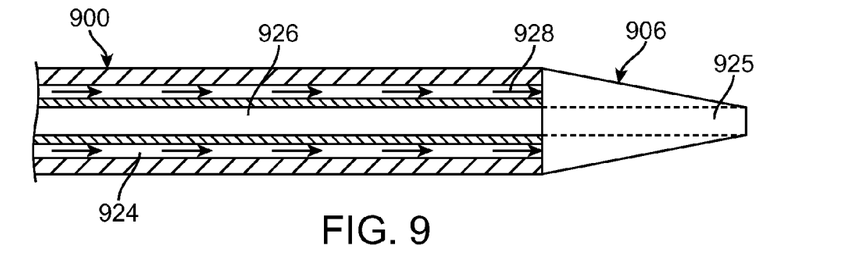
FIG. 9 is an alternate configuration of the catheter of FIG. 8.

Catheter 800 includes a guidewire lumen 826 such that catheter 800 may be tracked over a guidewire when being delivered to the treatment site. Lumen 826 is sized and shaped to slidingly accept a medical guidewire therethrough. It is desirable for lumen 826 to be as small as possible in order to minimize the crossing profile of catheter 800 such that it may fit within relatively small vessels. In the embodiment depicted in FIG. 8, catheter 800 is an extruded tubular shaft having dual lumens extending parallel or side-by-side along the full length thereof. Alternatively, the guidewire lumen may be formed by attaching an additional shaft to a single-lumen catheter (not shown). The additional shaft may be approximately the same length as the single-lumen catheter such that the catheter has a full over-the-wire configuration, or, as would be understood by one of ordinary skill in the art, may be substantially shorter than the full length of the single-lumen catheter and extend alongside only the distal portion of the single-lumen catheter in a rapid-exchange configuration. In yet another embodiment illustrated in FIG. 9, the guidewire lumen may be formed concentrically within the inflation lumen and be fluidly connected with a lumen extending through the detachable tip. As shown in FIG. 9, catheter 900 includes dual concentric lumens, inflation lumen 924 and guidewire lumen 926. Guidewire lumen 926 may extend the full length of catheter 900, or may extend only within the distal portion of catheter 900 in a rapid-exchange configuration. Guidewire lumen 926 is in fluid communication with a lumen 925 extending through detachable tip 906 such that the assembly may be delivered in an over-the-wire fashion. The concentric dual lumens of catheter 900 may be formed using an outer shaft and an inner shaft as is well known by one of ordinary skill in the art. As in the embodiment of FIG. 8, detachment tip 906 detaches from catheter 900 when pressure, as indicated by directional arrows 928, is provided through an inflation lumen 924 of catheter 900 via a pressure source (not shown) attached to the proximal end of the catheter.

Figure 10:
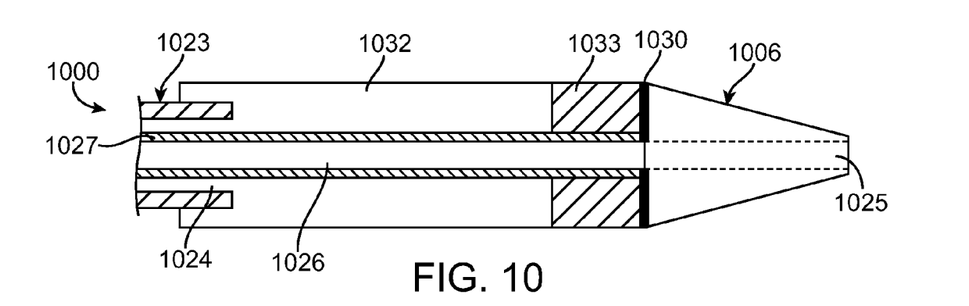
FIG. 10 is a schematic sectional view of a catheter having a deployment mechanism according to an embodiment of the present invention, wherein the deployment mechanism includes an inflatable balloon.
Figure 11:
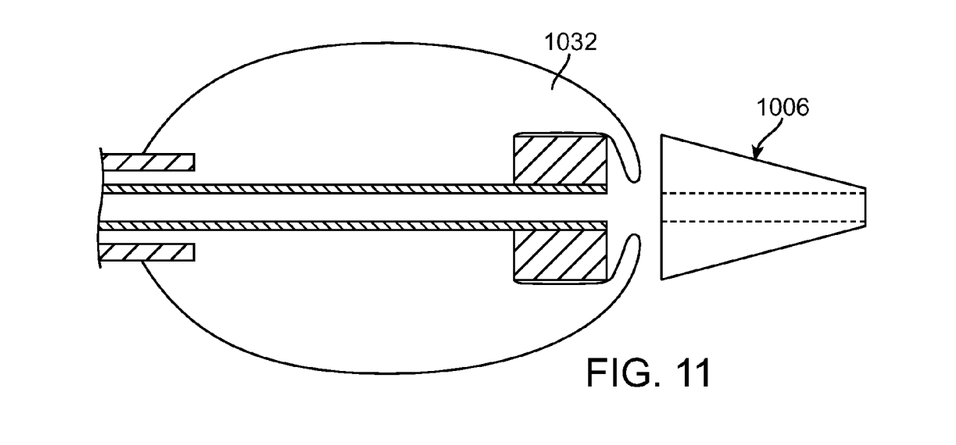
FIG. 11 illustrates the balloon of FIG. 10 in an inflated state.

In another embodiment, the deployment mechanism includes an inflatable balloon. As shown in FIGS. 10-11, catheter 1000 is a concentric dual lumen catheter having an inflatable balloon 1032 mounted at its distal end. In this embodiment, catheter 1000 includes an outer shaft 1023 and an inner shaft 1027, which extends through outer shaft 1023 and balloon 1032. An inflation lumen 1024 is defined between outer shaft 1023 and inner shaft 1027, and a guidewire lumen 1026 for receiving a guidewire is defined by inner shaft 1027. Guidewire lumen 1026 is in fluid communication with a lumen 1025 extending through detachable tip 1006 such that the assembly may be delivered in an over-the-wire fashion. An inflation fluid (not shown) for inflating balloon 1032 may be provided through inflation lumen 1024 of catheter 1000 via an inflation source (not shown) attached to the proximal end of the catheter. A tubular connector piece 1033 is shown for attaching balloon 1032 to inner shaft 1027, but balloon 1032 may be attached in any suitable manner known in the art.

Catheter 1000 also includes a detachable tip 1006 that is attached to catheter 1000 via a bond 1030. Bond 1030 may be formed with an adhesive, a solvent bond, a thermal bond, a connecting element between catheter 1000 and tip 1006, a room temperature vulcanised overcoat that cures over catheter 1000, or by another mechanical method. In an inflated configuration shown in FIG. 11, balloon 1032 radially and longitudinally expands. In order to expel tip 1006, balloon 1032 grows longitudinally to a position beyond bond 1030 such that balloon 1032 rolls out or extends over the surface of tip 1006 to cause failure of bond 1030 and forces tip 1006 off of the remainder of catheter 1000, thereby effectively detaching tip 1006 from catheter 1000 and leaving tip 1006 within the CTO. During inflation, balloon 1032 may be located within the CTO or may be located just proximal to the CTO, with tip 1006 extending within the CTO.

Figure 12:
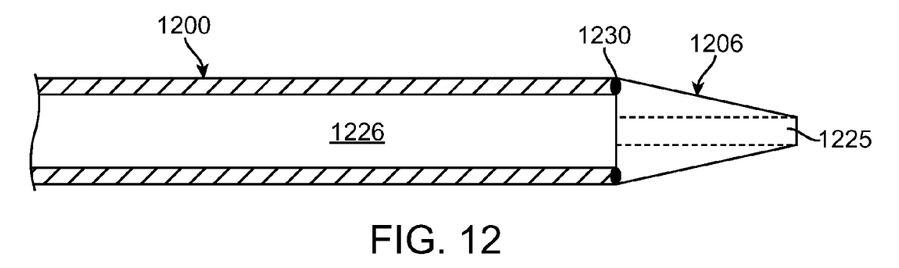
FIG. 12 is a schematic sectional view of a catheter having a deployment mechanism according to an embodiment of the present invention, wherein the deployment mechanism includes a temperature dependent adhesive.

In another embodiment depicted in FIG. 12, the deployment mechanism includes a temperature-dependent adhesive. As shown in FIG. 12, tip 1206 is attached to catheter 1200 via a bond 1230 constructed of a temperature-dependent adhesive. Once a particular temperature is reached, bond 1230 fails, effectively detaching tip 1206 from catheter 1200 and leaving tip 1206 within the CTO. In one embodiment, the temperature-dependent adhesive may include rapid cure acrylics such as cyanoacrylates that are thermoplastic in nature and will undergo adhesive failure at temperatures such around 60° C. Accordingly, bond 1230 would not fail until it reaches 60° C. In this embodiment, a localized heating source such as a heated fluid may be injected to raise the temperature of bond 1230 to 60° C., since a body temperature of approximately 37° C. would not alone cause bond failure. In another embodiment, the temperature-dependent adhesive may include materials that will undergo adhesive failure at body temperature, or approximately 37° C. A localized cooling source may be employed to keep tip 1206 at a temperature lower than 37° C. until it is tracked to the site of interest, thus preventing bond failure until tip 1206 is located within the CTO. Once properly in place, use of the cooling source is terminated and bond 1230 is permitted to acclimatize to 37° C. As shown in FIG. 12, catheter 1200 may include a single guidewire lumen 1226 in fluid communication with a lumen 1225 extending through detachable tip 1206 such that the assembly may be delivered in an over-the-wire fashion. Alternatively, the guidewire lumen may be formed as described above with respect to FIG. 8 such that the detachable tip is not required to have a lumen extending therethrough.

Figure 13:
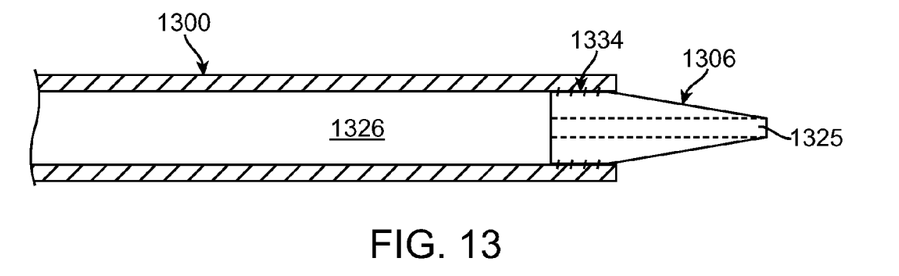
FIG. 13 is a schematic sectional view of a catheter having a deployment mechanism according to an embodiment of the present invention, wherein the deployment mechanism includes a screw-like attachment between the catheter and the tip.

In another embodiment, the deployment mechanism includes a screw-like attachment between the catheter and the tip. As shown in FIG. 13, tip 1306 includes one or more threads or protrusions 1334 and the distal end of catheter 1300 include mating indentations that are of such form, size, and spacing to mesh or cooperate with threads 1334. Tip 1306 is attached to catheter 1300 in a mechanical lock or screw-like manner. Tip 1306 is pushed into the lesion to effectively become lodged within a CTO. With tip 1306 embedded and stationary within the lesion, catheter 1300 is rotated to effectively detach tip 1306 from catheter 1300 and leave tip 1306 within the CTO. As such, tip 1306 simply "screws off" and is left embedded within the occlusion. As shown in FIG. 13, catheter 1300 may include a single guidewire lumen 1326 in fluid communication with a lumen 1325 extending through detachable tip 1306 such that the assembly may be delivered in an over-the-wire fashion. Alternatively, the guidewire lumen may be formed as described above with respect to FIG. 8 such that the detachable tip is not required to have a lumen extending therethrough.

Figure 14:
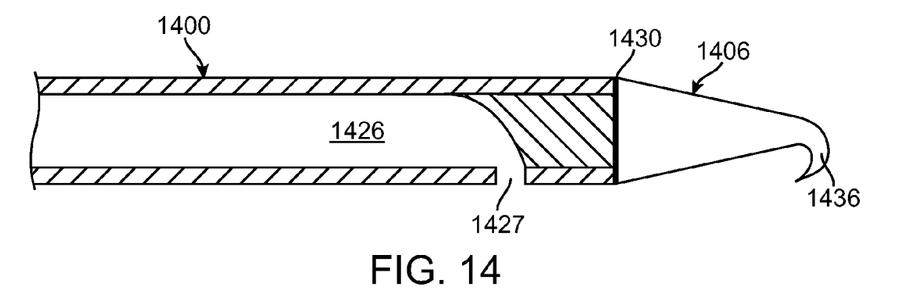
FIG. 14 is a schematic sectional view of a catheter having a deployment mechanism according to an embodiment of the present invention, wherein the deployment mechanism includes a hooked geometry of the tip.

In yet another embodiment, the deployment mechanism includes a hook-like tip geometry effective to lodge the tip within the CTO when the operator is retrieving the catheter. As shown in FIG. 14, tip 1406 includes a distal end 1436 having a curved or hook-like configuration. Tip 1406 is attached to catheter 1400 via a bond 1430. Bond 1430 may be formed with an adhesive, a solvent bond, a thermal bond, a connecting element between catheter 1400 and tip 1406, a room temperature vulcanised overcoat that cures over catheter 1400, or by another mechanical method. Tip 1406 is pushed into the lesion to effectively become lodged within a CTO via the geometry of hook-like distal end 1436. With tip 1406 embedded and stationary within the lesion, the operator applies a pulling force to catheter 1400 to break bond 1430, effectively detaching tip 1406 from catheter 1400 and leaving tip 1406 within the CTO. Although illustrated as a hook-like configuration, distal end 1436 may have a different geometry effective to lodge the detachable tip within the lesion such as a corkscrew or barbed configuration. As shown in FIG. 14, catheter 1400 may include a single guidewire lumen 1426 in fluid communication with a side port 1427 such that the assembly may be delivered in an over-the-wire or rapid exchange fashion. Further, additional embodiments described herein may also utilize a side port in fluid communication with a guidewire lumen such that the detachable tip is not required to have a lumen extending therethrough.

Figure 15:
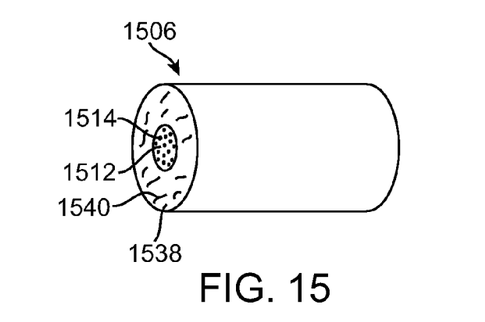
FIG. 15 is a schematic of a detachable tip according to another embodiment of the present invention, wherein the tip includes a layer for preventing restenosis.

In another embodiment of the invention, the detachable tip may include an additional layer or coating which releases a drug to prevent restenosis. For example, as depicted in FIG. 15, tip 1506 has a cylindrical configuration and includes two layers. The first or center layer includes a biodegradable polymer matrix 1512 having an active agent 1514 dispersed therethrough. Active agent 1514 is a therapeutic substance that softens or degrades the material of a CTO, and may be any substance described above with respect to active agent 114. The second or outer layer includes a biodegradable polymer matrix 1538 having an active agent 1540 dispersed therethrough. Active agent 1540 is a therapeutic substance that prevents restenosis. Suitable examples include, but are not limited to, antiplatelet agents, anticoagulant agents, antimicrobial agents, and antimetabolic agents. The layers are formed from different biodegradable materials. More particularly, biodegradable polymer matrix 1512 is formed from a first biodegradable material having a first dissolution rate. Biodegradable polymer matrix 1538 is formed from a second biodegradable material having a second dissolution rate. The second dissolution rate is slower than the first dissolution rate so that after active agent 1514 is released to clear the CTO, active agent 1540 is released to prevent restenosis. When located within the CTO, both layers of cylindrical tip 1506 are exposed to bodily fluids at the ends of the cylinder. Although the center layer degrades first, the CTO is not cleared instantaneously. Accordingly, the outer layer remains in contact with at least a portion of the lesion while active agent 1540 is released in order to prevent the remaining structure from embolizing.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A device for treatment of a chronic total occlusion, the device comprising:
    a catheter having a proximal end and a distal end;
    a detachable tip having a proximal end and a distal end, wherein the proximal end of the tip is attached to the distal end of the catheter such that the tip extends distally therefrom while the catheter is being advanced to the chronic total occlusion, the tip being formed of a biodegradable polymer with an active agent dispersed therethrough, the active agent being effective to degrade or soften at least a portion of the chronic total occlusion; and
    a detachment mechanism for detaching the tip from attachment with the distal end of the catheter, the detachment mechanism is a hooked distal end of the tip for lodging within the chronic total occlusion and holding the tip therein while the catheter is withdrawn thereby permitting the attachment between the tip and the distal end of the catheter to be broken.

2. The device of claim 1, wherein the biodegradable polymer is a solid material impregnated with the active agent.

3. The device of claim 1, wherein the active agent is dispersed within pores of the biodegradable polymer.

4. The device of claim 1, wherein the detachable tip has a frusto-conical shape.

5. The device of claim 1, wherein the active agent is selected from a group consisting of an enzyme, a drug, a bacteria, and a parasite.

6. The device of claim 1, wherein the detachable tip includes an outer layer of a second biodegradable polymer with a second active agent dispersed therethrough, the second active agent being effective to prevent restenosis.

7. The device of claim 1, wherein the detachment mechanism includes a fluid pressure source effective to break a bond between the detachable tip and the catheter.

8. The device of claim 1, wherein the detachment mechanism includes an inflatable balloon that is expandable to force the tip to detach from the distal end of the catheter.

9. The device of claim 1, wherein the tip is attached to the distal end of the catheter by a temperature dependent adhesive and the detachment mechanism is adhesive failure at a temperature at or above 37° C.

10. The device of claim 1, wherein a screw-like mating arrangement between the proximal end of the detachable tip and the distal end of the catheter attaches the tip to the catheter and the detachment mechanism is rotating the catheter to unscrew the tip.

11. A method of treating a chronic total occlusion, the method comprising the steps of:
    delivering a catheter to the chronic total occlusion, the catheter including a detachable tip bonded to a distal end of the catheter by one of an adhesive, a solvent bond, a thermal bond, and an overcoat the tip being formed from a biodegradable polymer with an active agent dispersed therethrough, the active agent being effective to degrade or soften at least a portion of the chronic total occlusion;
    advancing the detachable tip to a position within the occlusion;
    activating a detachment mechanism to break the bond between the tip and the distal end of the catheter detaching the tip from the catheter; and
    withdrawing the catheter while leaving the tip embedded within the chronic total occlusion.

12. The method of claim 11, further comprising the step of:
piercing the occlusion with the detachable tip.

13. The method of claim 11, wherein the tip is advanced through a previously formed channel within the chronic total occlusion.

14. The method of claim 11, wherein the active agent is selected from a group consisting of an enzyme, a drug, bacteria, and a parasite.

15. The method of claim 11, wherein the detachable tip includes an outer layer of a second biodegradable polymer with a second active agent dispersed therethrough, the second active agent being effective to prevent restenosis.

16. A device for treatment of a chronic total occlusion, the device comprising:

a catheter having a proximal end and a distal end;
a tip bonded to the distal end of the catheter such that the tip extends distally from the catheter distal end, the tip being formed out of a biodegradable polymer with an active agent dispersed therethrough, the active agent being effective to degrade or soften at least a portion of the chronic total occlusion; wherein the tip is bonded to the distal end of the catheter by one of an adhesive, a solvent bond, a thermal bond and an overcoat and
a detachment mechanism for breaking the bond between the tip and the distal end of the catheter to detach the tip therefrom.

17. The device of claim 16, wherein a lumen of the catheter is in fluid communication with a lumen defined by the tip.

\* \* \* \* \*